United States Patent
Rao et al.

(10) Patent No.: US 10,300,044 B2
(45) Date of Patent: May 28, 2019

(54) POLYMORPHIC FORMS OF METHYL((1S)-1-(((2S)-2-(5-(4'-(2-((2S)-1-((2S)-2-((METHOXYCARBONYL)AMINO)-3-METHYLBUTANOYL)-2-PYRROLIDINYL)-1H-IMIDAZOL-5-YL)-4-BIPHENYLYL)-1H-IMIDAZOL-2-YL)-1-PYRROLIDINYL)CARBONYL)-2-METHYLPROPYL) CARBAMATE AND SALTS THEREOF

(71) Applicant: Cipla Limited, Mumbai (IN)

(72) Inventors: Dharmaraj Ramachandra Rao, Mumbai (IN); Geena Malhotra, Mumbai (IN); Manjinder Singh Phull, Mumbai (IN); Shashirekha Kanathala, Mumbai (IN); Manish Gopaldas Gangrade, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 15/538,959

(22) PCT Filed: Dec. 24, 2015

(86) PCT No.: PCT/GB2015/054166
§ 371 (c)(1),
(2) Date: Jun. 22, 2017

(87) PCT Pub. No.: WO2016/102979
PCT Pub. Date: Jun. 30, 2016

(65) Prior Publication Data
US 2017/0354644 A1 Dec. 14, 2017

(30) Foreign Application Priority Data
Dec. 26, 2014 (IN) .......................... 4166/MUM/2014

(51) Int. Cl.
*A61K 31/4178* (2006.01)
*C07D 403/04* (2006.01)
*A61K 31/165* (2006.01)
*C07D 403/14* (2006.01)

(52) U.S. Cl.
CPC ........ *A61K 31/4178* (2013.01); *A61K 31/165* (2013.01); *C07D 403/04* (2013.01); *C07D 403/14* (2013.01)

(58) Field of Classification Search
None
See application file for complete search history.

(56) References Cited

U.S. PATENT DOCUMENTS 8,303,944 B2   11/2012   Bachand et al.
8,329,159 B2   12/2012   Belema et al.

FOREIGN PATENT DOCUMENTS

| EP | 2183244 B1 | 1/2013 |
|---|---|---|
| IN | 4166MUM2014 | 12/2014 |
| WO | 2015109445 A1 | 7/2015 |
| WO | 2016075588 A1 | 5/2016 |
| WO | 2016102979 A1 | 6/2016 |

OTHER PUBLICATIONS

Goho, A., "Tricky Business—The crystal form of a drug can be the secret to its success," Science News, Aug. 21, 2004, vol. 166, pp. 122-124, J. Am. Chem. Soc.
Haleblian, John K., "Characterization of Habits and Crystalline Modification of Solids and Their Pharmaceutical Applications," Journal of Pharmaceutical Sciences, vol. 64, No. 8, pp. 1269-1288, Aug. 1975.
Haleblian, John K., et al., "Pharmaceutical Applications of Polymorphism," Journal of Pharmaceutical Sciences, vol. 58, No. 8, pp. 911-929, Aug. 1969.
Kuhnert-Brandstaetter, M., "Polymorphie von Arzneistoffen und ihre Bedeuntung in der pharmazeutischen Technologie," Informationsdienst A.P.V., 1973, pp. 73-91.
Oetjen, G-W, "Freeze-Drying," Ullmann's Encyclopedia of Industrial Chemistry, 2012, vol. 16, pp. 51-101, Wiley-VCH Verlag GmbH & Co.
Reviriego, C., et al., "Daclatasvir dihydrochloride: treatment of hepatitis C virus HCV NS5A inhibitor," Drugs of the Future, 2011, vol. 36, No. 10, pp. 735-739, Prous Science.
Sohn, J.H., et al., "*Novosphingobium pentaromativorans* sp. nov., a high-molecular-mass polycyclic aromatic hydrocarbon-degrading bacterium isolated from estuarine sediment," International Journal of Systematic and Evolutionary Microbiology, 2004, vol. 54, pp. 1483-1487, IUMS.
Foreign communication from the priority application—International Search Report and Written Opinion, PCT/GB2015/054166, dated Mar. 10, 2016, 11 pages.

*Primary Examiner* — Samantha L Shterengarts
(74) *Attorney, Agent, or Firm* — Conley Rose, P.C.; Rodney B. Carroll (57) ABSTRACT

Amorphous methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate free base, amorphous methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate dihydrochloride, methods of making them, and pharmaceutical compositions containing them.

23 Claims, 5 Drawing Sheets

POLYMORPHIC FORMS OF METHYL((1S)-1-(((2S)-2-(5-(4'-(2-((2S)-1-((2S)-2-((METHOXYCARBONYL)AMINO)-3-METHYLBUTANOYL)-2-PYRROLIDINYL)-1H-IMIDAZOL-5-YL)-4-BIPHENYLYL)-1H-IMIDAZOL-2-YL)-1-PYRROLIDINYL)CARBONYL)-2-METHYLPROPYL) CARBAMATE AND SALTS THEREOF

CROSS REFERENCE TO RELATED APPLICATIONS

This application is a filing under 35 U.S.C. 371 of International Application No. PCT/GB2015/054166 filed Dec. 24, 2015, entitled "Polymorphic Forms of Methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate and Salts Thereof" which claims priority to Indian Patent Application No. 4166/MUM/2014 filed Dec. 26, 2014, which applications are incorporated by reference herein in their entirety.

FIELD OF INVENTION

The present invention relates to a novel polymorphic form of methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate and pharmaceutically acceptable salts thereof and processes thereof.

The invention is also directed to pharmaceutical compositions containing at least one polymorphic form and to the therapeutic or prophylactic use of such polymorphic forms and compositions.

BACKGROUND OF THE INVENTION

Pharmaceutical solids can exist in different crystal forms, such as crystalline, amorphous, or glass and also in solvated or hydrated states (Haleblian et al., 1969, 1975; Kuhnert-Brandstaetter, 1973; Sohn 2004). Polymorphism is the ability of any element or compound to crystallize as more than one distinct crystal species.

It is a well known fact that different polymorphic forms of the same drug may have substantial differences in certain pharmaceutically-important physicochemical properties, such as stability, solubility, dissolution rate, crystal habit, tableting behavior. Changes in certain of these physiochemical properties may ultimately affect the bioavailability of the drug. Furthermore, different physical forms may have different particle size, hardness and glass transition temperatures. In certain cases, this phenomenon may affect the quality and performance of the final dosage form.

Regulatory authorities desire to have all possible polymorphic forms of a new drug substance identified prior to approval of a product containing the drug. However, as is well known in the art, the existence of polymorphic forms of any given compound cannot be predicted, and there is no standard procedure for proceeding to make a previously unknown polymorphic form. Even after a polymorph has been identified, there is no possibility of predicting whether any additional forms will ever be discovered. This has been described in many recent articles, including A. Goho, *Science News*, Vol. 166, No. 8, pages 122-123 (August 2004).

The compound, methyl((1 S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate (also referred to as "Compound A"), Compound A is a drug for the treatment of hepatitis C (HCV). It was developed by Bristol-Myers Squibb and was approved in Europe on 22 Aug. 2014. Compound A is also known as daclatasvir (also referred to as daclatasvir in free base form or daclatasvir free base).

The compound A as well as pharmaceutically acceptable salts thereof, are described in U.S. Pat. Nos. 8,303,944 and 8,329,159, the disclosures of which are hereby incorporated in their entireties by reference for all purposes. This compound inhibits the HCV nonstructural protein NS5A. Recent research suggests that it targets two steps of the viral replication process, enabling rapid decline of HCV RNA.

Compound A is a chiral molecule with four stereocenters (1,1',2,2') in the S configuration.

Polymorphism has been observed for methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl) carbamate dihydrochloride (also referred to as "Compound B" or daclatasvir dihydrochloride).

Compound B

Although two neat (wholly) crystalline dihydrochloride salts, N-1 and N-2 of compound B have been identified in screening studies (N-2 being claimed in EP2183244), it has been confirmed that the form N-2 is the thermodynamically most stable polymorph. The N-2 form of compound B remained unchanged during storage under long-term or accelerated conditions and only this form is produced by the proposed synthetic process.

Compound A is used in the treatment of hepatitis C (HCV). This disease primarily affects the liver and the infection is often asymptomatic but the chronic infection can ultimately lead to cirrhosis which in some cases may develop liver failure, liver cancer or life threatening esophageal and gastric varices. Consequently, it would be a significant contribution to the art to provide novel forms of compound A and pharmaceutically acceptable salts thereof, having advantageous properties, and methods of preparation, pharmaceutical formulations, and methods of use thereof.

OBJECTS OF THE INVENTION

An object of the present invention is to provide various polymorphic forms of compound A and pharmaceutically acceptable salts thereof.

A further object of the present invention is to provide a polymorphic form of compound A and a polymorphic form of compound B.

Another object of the present invention is to provide processes for the preparation of novel polymorphic forms of compound A (and pharmaceutically acceptable salts thereof) and compound B.

Yet another object of the invention is to provide a pharmaceutical composition comprising a therapeutically effective amount of novel forms of compound A and pharmaceutically acceptable salts thereof.

Yet another object of the invention is to provide a method of treatment of diseases or symptoms of HCV, wherein novel forms of compound A and pharmaceutically acceptable salts thereof, are useful.

SUMMARY OF THE INVENTION

In one aspect, the present invention provides methyl((1S)-1-(((2S)-2-(5-(4'-(2-((2S)-1-((2 S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate in an amorphous form.

In another aspect, the present invention provides a novel amorphous polymorphic form of compound A (daclatasvir) and a novel amorphous pharmaceutically acceptable dihydrochloride salt thereof (compound B). These novel forms may exhibit enhanced solubility in water, permeability, bioavailability and may be suitable for bulk handling and formulating into a formulation.

Figure 1:
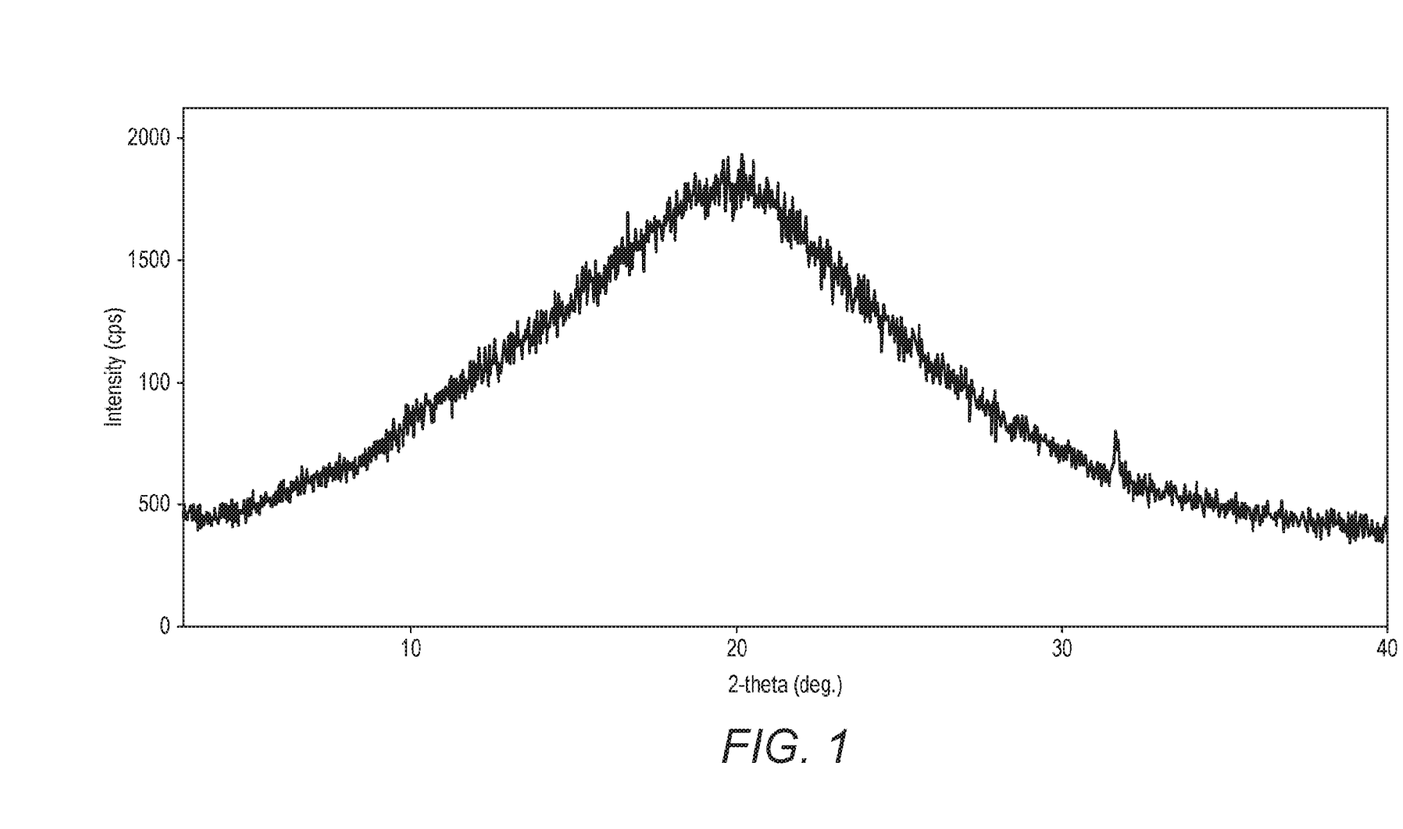
FIG. 1 is the X-ray powder diffractogram (XRPD) of amorphous Form A of compound A.

In another aspect, the present invention provides an amorphous form of compound A designated as "Form A". Form A may be characterized by its powder X-ray diffraction pattern, as shown in FIG. 1. Further Form A may be at least (or more than) about 50%, 75%, 90%, 95%, 96%, 97%, 98%, 99 or 100% amorphous, based on the total weight of the compound. Preferably Form A is wholly amorphous, that is about 100% amorphous. Alternatively, Form A is preferably at least about 90-99% amorphous or about 95-99% amorphous, preferably about 90%, 91%, 92%, 93%, 94%, 95%, 96%, 97%, 98%, 99% amorphous.

Figure 2:
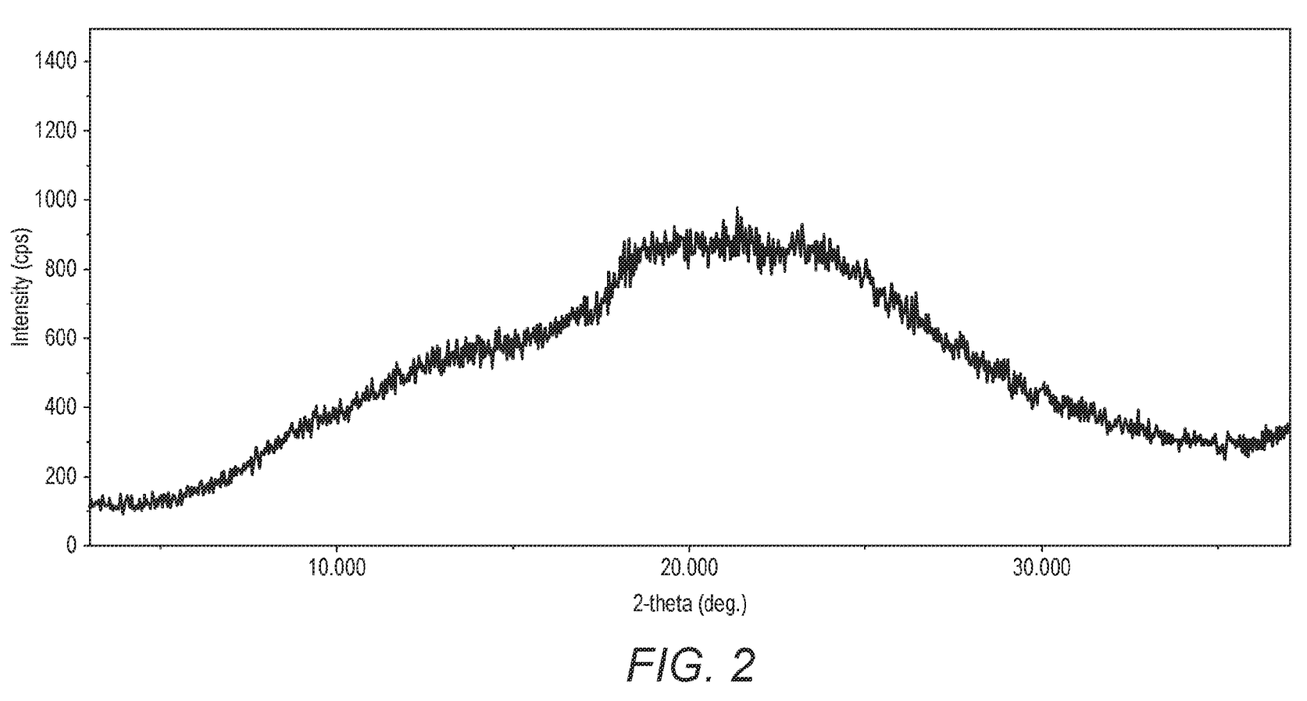
FIG. 2 is the X-ray powder diffractogram (XRPD) of amorphous Form C of compound B.
Figure 3:
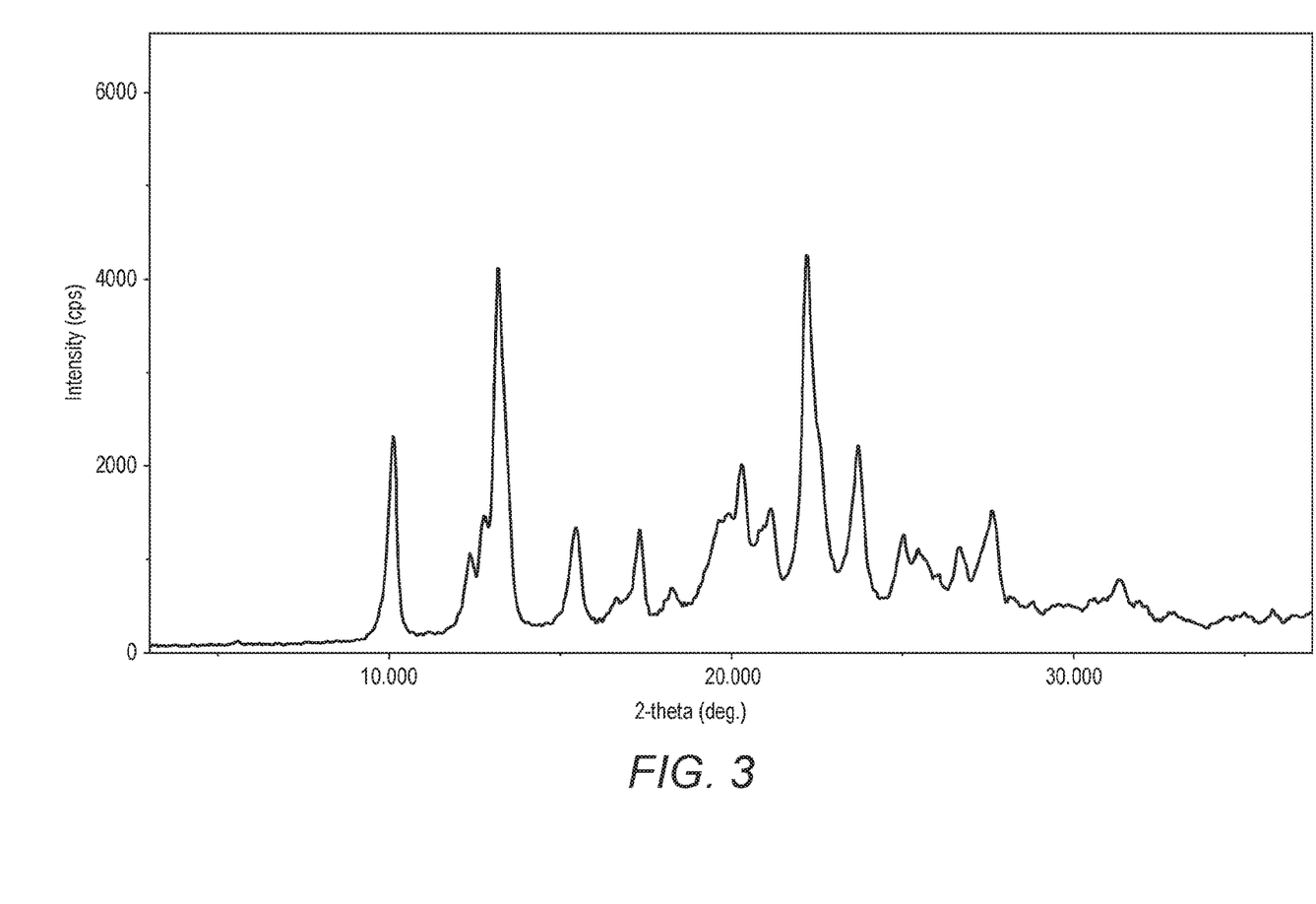
FIG. 3 is the X-ray powder diffractogram (XRPD) of crystalline Form N-2 of compound B.

According to another aspect of the present invention, there is provided an amorphous form of compound B designated as "Form C". Form C may be characterized by its powder X-ray diffraction pattern, as shown in FIG. 2. Form C may be at least about 50%, 75%, 90%, 95%, 96%, 97%, 98%, 99% or 100% amorphous, based on the total weight of the compound. Preferably Form C is wholly amorphous, that is about 100% amorphous. Alternatively, Form C is preferably at least about 90-99% amorphous or about 95-99% amorphous, preferably about 90%, 91%, 92%, 93%, 94%, 95%, 96%, 97%, 98%, 99% amorphous.

In another aspect, the invention provides processes for preparing these novel forms. These processes may result in the novel forms having high purity (HPLC purity). For example the high purity may be above about 99.0%, 99.1%, 99.2%, 99.3%, 99.4% and preferably above about 99.5% purity, for example about 99.5%, 99.6%, 99.7%, 99.8%, 99.9% or 100% purity. These processes may also result in the novel forms having high yield.

In another aspect, the present invention provides processes for preparing amorphous methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate free base.

In a further aspect, the present invention provides processes for amorphous methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate dihydrochloride.

The advantages of the processes of the present invention include simplicity of manufacturing (which is also industrially advantageous), eco-friendliness, cost effectiveness and suitability for commercial use. Further they advantageously provide highly pure compound A and compound B, both in high yields.

In another aspect, the present invention further provides processes for inter-conversion of amorphous forms to crystalline forms and inter-conversion of crystalline forms.

In another aspect, the present invention provides a pharmaceutical composition comprising methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate in an amorphous form.

In another aspect, the present invention also provides methods for preparing a pharmaceutical composition comprising a novel form of compound A and/or a pharmaceutically acceptable salt thereof (for example compound B), together with one or more pharmaceutically acceptable excipients carriers or diluents.

The present invention further provides a method of treatment of diseases or symptoms of HCV wherein compound A and pharmaceutically acceptable salts thereof, are useful.

In another aspect, the present invention provides therapeutic uses and therapeutic methods of treatment employing the compositions comprising amorphous daclatasvir (Form A) and/or amorphous daclatasvir dihydrochloride (Form C).

DETAILED DESCRIPTION

Unless otherwise indicated, this disclosure uses definitions provided below.

"About," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

"Pharmaceutically acceptable" refers to substances, which are within the scope of sound medical judgment, suitable for use in contact with the tissues of subjects without undue toxicity, irritation, allergic response, and the like, commensurate with a reasonable benefit/risk ratio, and effective for their intended use.

"Treating" refers to reversing, alleviating, inhibiting or slowing the progress of, or preventing a disorder or condition to which such term applies, or to preventing one or more symptoms of such disorder or condition.

"Treatment" refers to the act of "treating."

"Drug," "drug substance," "active pharmaceutical ingredient," and the like, refer to a compound that may be used for treating a subject in need of treatment.

"Excipient" or "adjuvant" refers to any component of a pharmaceutical composition that is not the drug substance.

"Drug product," "pharmaceutical dosage form," "final dosage form," and the like, refer to the combination of one or more drug substances and one or more excipients (i. e., pharmaceutical composition) that is administered to a subject in need of treatment, and may be in the form of tablets, capsules, liquid suspensions, patches, and the like.

"Inert" refers to substances that may positively influence the bioavailability of the drug, but are otherwise unreactive.

"Amorphous" refers to any solid substance which (i) lacks order in three dimensions, or (ii) exhibits order in less than three dimensions, order only over short distances (e.g., less than 10 Å), or both. Thus, amorphous substances include partially crystalline materials and crystalline mesophases with, e.g. one- or two-dimensional translational order (liquid crystals), orientational disorder (orientationally disordered crystals), or conformational disorder (conformationally disordered crystals). Amorphous solids may be characterized by known techniques, including X-ray powder diffraction (XRPD) crystallography, solid state nuclear magnet resonance (ssNMR) spectroscopy, differential scanning calorimetry (DSC), or some combination of these techniques. As illustrated, below, amorphous solids give diffuse XRPD patterns (i.e., is not crystalline as determined by XRPD), typically comprised of one or two broad peaks (i.e., peaks having base widths of about 5° 2θ or greater). Amorphous solids exhibit a characteristic amorphous halo in an XRPD pattern. An amorphous halo is a term of art which is known to refer to the characteristic broad and diffuse peak shape (made up of one or two broad peaks) distributed in a wide range 2θ. This characteristic peak shape is as a result of the lack of order in the amorphous structure and contrasts significantly to the sharp characteristic peaks of an ordered crystalline structure.

The present invention provides a novel amorphous form of compound A and a novel amorphous form of compound B, methods of preparing the novel forms of compound A and compound B and pharmaceutical compositions comprising them. The novel forms may advantageously have high purity and/or yield. For example the purity of the forms may be above about 99.0%, 99.1%, 99.2%, 99.3%, 99.4% and preferably above about 99.5% purity, for example about 99.5%, 99.6%, 99.7%, 99.8%, 99.9% or 100% purity. The advantages of the process include simplicity in manufacturing, eco-friendliness and suitability for commercial use.

As polymorphic forms are most reliably characterized primarily by peak positions in the X-ray diffractogram, the polymorphs of the present invention have been characterized by X-ray powder diffraction (XRPD) crystallography which produces a fingerprint of the particular form. In other words, each of the new polymorphic forms is differentiated by a unique X-ray powder diffraction pattern.

All the powder diffraction patterns were measured on a Rigaku Model Smart Lab and Rigaku Model Miniflex X-ray powder diffractometer with a copper-K-α radiation source. The XRD pattern is expressed in terms of 2 theta values (2θ) and percentage intensity (%).

The amorphous nature of Form A of compound A has been analyzed, characterized and differentiated by X-ray powder diffraction, a technique which is known per se.

Preferably the amorphous Form A of compound A of the present invention is characterized by having an X-ray powder diffraction pattern as shown in FIG. 1.

Preferably the amorphous Form A of compound A of the present invention is characterized by its X-ray powder diffraction pattern comprising an amorphous halo. Preferably the X-ray diffraction pattern does not comprise any sharp (or distinct) characteristic peaks.

The amorphous Form A of compound A according to (or obtained by) the present invention is substantially free (or free or essentially free) from other crystal and/or non-crystal forms of compound A, for example free from crystalline forms of compound A. "Substantially free" or "Essentially free" from other forms of compound A shall be understood to mean that the polymorph of compound A contains less than about 10%, 9%, 8%, 7%, 6% or preferably less than about 5%, of any other forms of compound A (for example crystalline forms) and preferably less than about 1% (for example less than about 0.9, 0.8, 0.7, 0.6, 0.5, 0.4, 0.3, 0.2 or 0.1%) of other impurities, water or solvates (wherein all percentages are based on the total weight of the compound). Preferably Form A is solvate free.

Those skilled in the art would recognize that Form A may be characterized by other methods including, but not limited to IR, solid state NMR and Raman spectroscopy.

The amorphous form A of compound A of the present invention was further characterized by IR spectroscopy. This was carried out on a Bruker Model: Alpha Fourier Transform Infrared (FTIR) Spectrometer.

Figure 4:
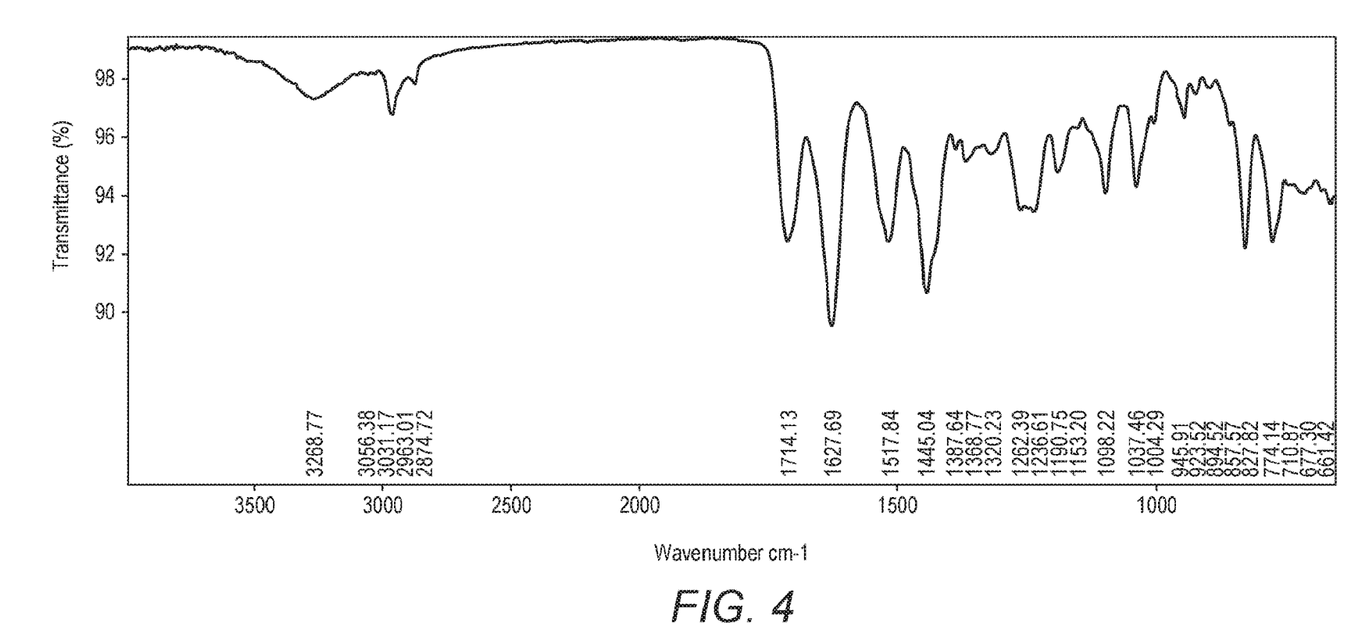
FIG. 4 is the Fourier Transform Infrared (FTIR) spectrum of amorphous Form A of compound A.

Accordingly, the amorphous form A of compound A of the present invention can be characterized as having a FTIR spectrum as shown in FIG. 4.

All the polymorphs obtained in the present invention are stable, highly pure and have low amounts of residual solvents (in other words, conforming with the ICH limit for residual solvents).

In one aspect, the present invention provides a stable amorphous polymorph of compound A which is hereinafter designated as 'Form A' which is substantially non-hygroscopic (or non-hygroscopic) and has good flow characteristics. In particular, the Form A of compound A may exhibit advantageous intrinsic dissolution.

Pharmaceutical compositions according to the present invention comprise amorphous Form A of Compound A as an active ingredient, together with one or more pharmaceutically acceptable carriers, excipients or diluents.

In another aspect, the present invention provides a process for preparing the novel Form A of compound A. Preferably, Form A is solvate-free. The process also produces amorphous Form A of compound A with high yield and purity.

In another aspect, the present invention provides a process for the preparation of amorphous Form A of compound A. The compound A used in preparing the polymorph may be obtained by methods described in the prior art which are herein incorporated by reference in their entirety. The compound A used as a starting material can be in any form, e.g. it can be in a reaction solution, suspension, crude or in anhydrous, hydrated or solvated form. Thus, one advantage of using amorphous Form A is that it may be prepared without having to purify the starting material.

Amorphous Form A may be prepared by a process (method A1) comprising the steps of:
i. condensing N-methoxy carbonyl-L-valine [MOC-L-Valine] with 5,5'-(4,4'-biphenyldiyl)bis(2-((2S)-2-pyrrolidinyl)-1H-Imidazole.Hydrochloride [DCV imidazole HCl] using a condensing reagent or mixture of condensing reagents thereof in a suitable inert organic solvent in a suitable base at a suitable temperature,
ii. adding a first solvent,
iii. separating the organic layer or filtering the solid, for example by washing with NaCl and NaOH solutions
iv. optionally filtering, preferably over hyflo (Celite® Analytical Filter Aid), and optionally washing with the first solvent
v. optionally drying, preferably over a drying agent,
vi. optionally concentrating, preferably under vacuum,
vii. optionally stripping off with a second solvent, or dissolving in a second solvent (in other words removing the first solvent/removing the first solvent and replacing with a second solvent),
viii. isolating the precipitated amorphous Form A of compound A and,
ix. drying the precipitated amorphous Form A.

Amorphous Form A may also be prepared by a process (method A2) comprising the steps of:
i. dissolving compound A of any form, or in a mixture of any forms, in a first solvent, and optionally heating while stirring at a temperature ranging from about 30-90° C. (preferably about 40-80° C., about 50-70° C., more preferably about 60° C.), followed by cooling, preferably to room temperature,
ii. optionally filtering, preferably over hyflo,
iii. optionally drying, preferably over a drying agent,
iv. optionally concentrating, preferably under vacuum,
v. optionally adding a second solvent (stripping off with second solvent, or dissolving in second solvent),
vi. isolating the precipitated amorphous Form A of compound A and,
vii. drying the precipitated amorphous Form A.

Amorphous Form A may also be prepared by a process (method A3) comprising the steps of:
i. dissolving compound A of any form, or in a mixture of any forms, in a first solvent, and optionally heating while stirring at a temperature ranging from about 30-90° C. (preferably about 40-80° C., about 50-70° C., more preferably about 60° C.), followed by cooling, preferably to room temperature
ii. optionally filtering, preferably over hyflo,
iii. optionally drying, preferably over a drying agent,
iv. adding a second solvent,
v. isolating the precipitated amorphous Form A of compound A and,
vi. drying the precipitated amorphous Form A.

Amorphous Form A may also be prepared by a process (method A4) comprising the steps of:
i. dissolving compound B of any form, or in a mixture of any forms, in a first solvent,
ii. adjusting the pH of the reaction mass using a base
iii. extracting the reaction mass with a first solvent (this first solvent can be the same or different to the first solvent solvent used in step (i) of this process)
iv. optionally drying, preferably over a drying agent
v. distilling the obtained organic layer, preferably under reduced pressure
vi. optionally adding a second solvent (in other words stripping off with a second solvent, or dissolving in a second solvent)
vii. optionally isolating the precipitated amorphous Form A of compound A and,
viii. drying the precipitated amorphous Form A.

Amorphous Form A may also be prepared by a process (method A5) comprising the steps of:
i. condensing MOC-L-Valine with DCV imidazole HCl using a condensing reagent or mixture of condensing reagents thereof in a suitable inert organic solvent in a suitable base at a suitable temperature,
ii. quenching the reaction mass, preferably in NaOH solution,
iii. stirring, preferably for about 15 minutes to 1 hour, preferably for about 15-45 minutes, preferably for about 30 minutes at a suitable temperature, such as about 15-50° C., preferably about 25-30° C.,
iv. isolating the precipitated amorphous Form A of compound A,
v. drying the precipitated amorphous Form A.

The obtained compound A (obtained from any of the processes above) may further be purified using a first solvent or a second solvent or a mixture thereof (these solvents preferably are the same as those used in the processes above).

The first solvent that can be used for dissolution in these above preparations include water; alcohols comprising methanol, ethanol, isopropanol, N-butanol; ketones comprising acetone, methyl ethyl ketone; chloroalkanes, comprising dichloromethane (MDC); alkyl alkanoates comprising methyl acetate, ethyl acetate, butyl acetate, isopropyl acetate and a mixture thereof. Preferably the first solvent is water, an alcohol, a ketone, a chloroalkane, an alkyl alkanoate or any combination thereof. More preferably the solvent is water, an alcohol or alkyl alkanoate or any combination thereof. Most preferably, the first solvent is ethyl acetate, isopropyl acetate, methanol or water or any combination thereof.

The second solvent used may be an anti solvent wherein the anti solvent is selected from water, alcohols comprising methanol, ethanol, isopropanol, N-butanol; dialkyl ethers comprising diisopropyl ether, methyl t-butylether; aromatic hydrocarbons comprising toluene, xylene, and aromatic chlorohydrocarbons comprising chlorobenzene, 1,2-dichlorobenzene, dichloromethane (MDC); hydrocarbons comprising n-pentane, n-hexane, n-heptane, cyclopentane, cyclohexane and a mixture thereof. Preferably, the second solvent is water, an alcohol, a dialkyl ether, an aromatic hydrocarbon, an aromatic chlorohydrocarbon, a hydrocarbon or any combination thereof. More preferably, the second solvent is n-heptane or water.

A suitable condensing reagent for use in a process according to the present invention can be selected from the group comprising of phenylsilane, 1,1'-carbonyldiimidazole (CDI), benzotriazol-1-yloxytris (dimethylamino) phophonium hexafluorophosphate (BOP), 1-hydroxy benzotriazole hydrate (HOBt), PyBOP (Analog of the BOP), 1,3-dicyclohexylcarbodiimide (DCC), N-Ethyl-N'-(3-dimethylaminopropyl)carbodidimide hydrochloride (EDC HCl), (1-[Bis (dimethyl amino)methylene]-1H-1,2,3-triazolo[4,5-b] pyridinium 3-oxid hexafluoro phosphate) (HATU), chloroformates such as ethyl chloroformate or isobutyl chloroformate. These agents act in situ as activating reagents and convert the carboxylic acids to more reactive intermediates. Alternatively, phenylsilane, SOCl2, POCl3 and PCl3 can act as an in situ carboxylic acid activating agents, and can be effectively used as a coupling reagent to prepare carboxamides. Preferably the condensing agent(s) is HOBt and/or EDC.HCl.

By "inert organic solvent" is meant an organic solvent, which under the reaction conditions of a process according to the present invention, does not react with either the reactants or the products. A suitable inert organic solvent for use in a process according to the present invention can be selected from the group consisting of dimethylformamide (DMF), dimethylacetamide (DMA), dimethyl sulfoxide (DMSO), N-methyl pyrrolidone (NMP), sulfolane, diglyme, 1,4-dioxane, tetrahydrofuran (THF), acetonitrile, acetone, dichlromethane (MDC), toluene, xylene and any combination thereof and other inert organic solvents known in the art. Preferably the "inert organic solvent" is acetonitrile or DMF.

A suitable base to be used in a process of the present invention may be an organic base and/or an inorganic base. Preferably the organic base is an aliphatic or aromatic organic base and preferably the inorganic base is an alkali metal carbonate, alkali metal alkoxide or alkali metal hydroxide inorganic base and any combination thereof.

Suitable organic bases can be selected from the group comprising of aliphatic or aromatic bases and can be selected from, but not limited to triethyl amine, diisopropyl amine, diisopropyl ethyl amine (Hunig's base), pyridine, picoline, diethyl amine, piperidine and any combination thereof. Preferably the organic base is diisopropyl ethyl amine.

Suitable inorganic bases can be selected from the group comprising of ammonia, alkali metal carbonates, such as cesium carbonate, sodium carbonate, sodium bicarbonate, potassium carbonate; alkali metal alkoxide such as sodium methoxide, sodium ethoxide, potassium tertiary butoxide; alkali metal hydroxides such as sodium hydroxide, potassium hydroxide and any combination thereof.

The base used for adjusting the pH in method A4 above is preferably an inorganic base as mentioned above, preferably ammonia. The pH would also preferably be adjusted to between about 6 and 9, preferably about 7.5.

The condensation is suitably carried out at a temperature ranging from about 5° C. to the boiling point of the reaction mass until no starting material is detectable. Preferably, the temperature is about 5 to 30° C., preferably about 20 to 30° C. or about 10 to 15° C. Preferably, the condensing is carried out under a nitrogen atmosphere.

The drying agents that can be used for the removal of water include but are not limited to anhydrous sodium sulphate, anhydrous magnesium sulphate, anhydrous zinc chloride and anhydrous calcium chloride. Preferably, the drying agent is anhydrous sodium sulphate.

The isolation may be carried out by filtering, decanting or centrifuging.

The final drying step of the processes described above is preferably carried out at a temperature ranging from about 30 to 80° C. preferably from about 30 to 60° C., about 25 to 55° C., more preferably about 40 to 45° C. or about 35 to 40° C., typically for a period of time ranging from about 2 to 30 hours, preferably 4 to 20 hours. Further, the final drying step is preferably carried under reduced pressure, for example in a vacuum.

Alternatively, amorphous Form A may be prepared from crystalline compound A (or suitable precursor) by methods that involve rapid removal of a solvent from a mixture or cooling a molten sample. Such methods include, but are not limited to rotational evaporation, vacuum drying, melt congealing, melt extrusion, spray drying, spray coating, lyophilization, and other methods. Spray drying and spray coating both involve dissolving compound A in a compatible solvent as described above to form a solution. A compatible solvent is any liquid which will dissolve compound A, atomizing the resulting solution, and evaporating the solvent to form drug substance comprised of amorphous Form A. Additional processing, such as tray-drying, may be required to meet ICH residual solvent levels.

Amorphous Form A may also be made by spray coating or layering amorphous Form A onto a core. Spray coating includes dissolving crystalline compound A in a compatible solvent as described above to form a solution and atomizing the resulting solution into droplets which are sprayed onto a core.

The core may be pharmaceutically inert and is mainly intended for carrying the layer or layers of amorphous Form A. The core may be a solid particle or may comprise a disintegrating agent. Examples of core materials are nonpareil seeds, sugar beads, wax beads, glass beads, lactose, microcrystalline cellulose, polymer beads, starch, colloidal silica, etc. Alternatively, the core may be a dosage form such as a tablet, pill, multiparticulate or capsule, which may contain compound A or a different drug. Spray coating amorphous Form A onto the dosage form may be useful for a combination therapy of compound A along with another drug.

Lyophilization or freeze drying also involves dissolving compound A in a compatible solvent as described above, and includes rapidly freezing the solution to form amorphous Form A and removing the solvent via sublimation (typically under vacuum) and desorption. For more detailed description of lyophilization, see Georg-Wilhelm Oetjen, "Freeze-Drying," *Ullmann's Encyclopedia of Industrial Chemistry* (2012).

Alternatively, amorphous Form A may be prepared using any pharmaceutically acceptable form of Compound A, including its free base and its pharmaceutically acceptable complexes, salts, solvates, and hydrates.

For each of these methods, the fraction of drug substance of Form A that is amorphous is in the range of about 50% w/w to about 100% w/w, 75% w/w to about 100% w/w, 90% w/w to about 100% w/w, or about 95% w/w to about 100% w/w, based on the total mass of compound A. Ideally, the fraction of compound A that is amorphous is in the range of about 99% w/w to about 100% w/w, based on the total mass of compound A.

The amorphous Form A of compound A according to (or obtained by) the present invention is substantially free (or free or essentially free) from other crystal and/or non-crystal forms of compound A, for example free from crystalline forms of compound A. "Substantially free" or "Essentially free" from other forms (polymorphs) of compound A shall be understood to mean that the polymorph of compound A contains less than about 10%, 9%, 8%, 7%, 6% or preferably less than about 5%, of any other forms of compound A (for example crystalline forms) and preferably less than about 1% (for example less than about 0.9, 0.8, 0.7, 0.6, 0.5, 0.4, 0.3, 0.2 or 0.1%) of other impurities, water or solvates (wherein all percentages are based on the total weight of the compound). Preferably Form A is solvate free.

Form A of compound A obtained by any of the processes described herein may further be purified using the first solvent or the second solvent or a mixture thereof.

The process of the invention may be used as a method for purifying any form of compound A, as well as for the preparation of the new polymorphic forms or pharmaceutically acceptable salts thereof of compound A or compound B.

Thus, another aspect of the present invention is directed to the use of amorphous Form A of compound A, as a starting material for the preparation of the crystalline, hydrate or anhydrous compound A or compound B.

The pharmaceutically acceptable salts can be prepared during the final isolation and purification of the compounds or separately by reacting a suitable nitrogen atom with a suitable acid. Useful salts may include acid addition salts (including di-acids) including but not limited to nontoxic salts derived from inorganic acids such as hydrochloric acid, nitric acid, phosphoric acid, sulfuric acid, hydrobromic acid, hydroiodic acid, hydrofluoric acid, and phosphorous acids, dihydrobromide, dihydrochloride, dihydroiodide, as well as nontoxic salts derived from organic acids, such as but not limited to aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, alginate, aspartate, benzoate, besylate, bicarbonate, bisulfate, butyrate, borate, carbonate, camsylate, citrate, cyclamate, camphorate, digluconate, edisylate, esylate, formate, fumarate, gluceptate, gluconate, glucuronate, glycerophosphate, fonnate, fumarate, hexafluorophosphate, hemisulfate, hibenzate, hydrochloride, hydrobromide, hydroiodide, heptanoate, hexanoate, 2-hydroxyethanesulfonate, isethionate, lactate, malate, maleate, malonate, mesylate, methylsulfate, mesitylenesulfonate, naphthylate, 2-napsylate, nicotinate, nitrate, orotate, oxalate, palmitate, pamoate, palmoate, pectinate, persulfate, phosphate, 3-phenylproprionate, picrate, pivalate, propionate, hydrogen phosphate, dihydrogen phosphate, pyroglutamate, saccharate, stearate, sulfate, succinate, tannate, tartrate, tosylate, trichloroacetate, trifluoroacetate, para-toluenesulfonate, undecanoate and xinofoate salts.

In still another aspect, the present invention provides a stable amorphous polymorphic form of compound B which is hereinafter designated as 'Form C' which is substantially non-hygroscopic (or non-hydroscopic) and has good flow characteristics. In particular, the amorphous Form C of compound B has comparable intrinsic dissolution, when compared to prior art forms of compound B (e.g. form N-2 of compound B).

The following data illustrates the intrinsic dissolution of daclatasvir dihydrochloride form N-2 when compared to amorphous Form C of the present invention (i.e. amorphous Form C of daclatasvir dihydrochloride).

TABLE 1

| Time in minutes | % Release of Form N-2 daclatasvir dihydrochloride (Form N-2 of compound B) | % Release of Amorphous form of daclatasvir dihydrochloride (Form C of compound B of the present invention) |
|---|---|---|
| 5 | 15 | 14 |
| 15 | 60 | 60 |
| 30 | 77 | 74 |
| 60 | 82 | 81 |
| 120 | 84 | 82 |
| 240 | 86 | 84 |
| 360 | 87 | 82 |
| 480 | 85 | 80 |
| 600 | 86 | 80 |
| 720 | 86 | 80 |

Table 1 Experimental conditions:
Dissolution medium: 0.1 N HCl
Temperature: 37±0.5° C.
Rotation speed: 50 rpm

TABLE 2

| Time in minutes | % Release of Form N-2 daclatasvir dihydrochloride | % Release of Amorphous form of daclatasvir dihydrochloride (Form C of compound B of the present invention) |
|---|---|---|
| 5 | 55 | 55 |
| 15 | 92 | 88 |
| 30 | 100 | 99 |
| 60 | 102 | 101 |
| 120 | 103 | 103 |
| 240 | 103 | 102 |
| 360 | 101 | 97 |
| 480 | 107 | 102 |
| 600 | 103 | 103 |
| 720 | 103 | 99 |

Table 2 Experimental conditions:
Dissolution medium: 50 mM potassium phosphate buffer at pH 8.6 with 0.75% brij 35
Temperature: 37±0.5° C.
Rotation speed: 75 rpm The above data indicates that the intrinsic dissolution of both form N-2 and the amorphous Form C of the present invention are comparable.

The amorphous Form C of compound B of the present invention (daclatasvir dihydrochloride) preferably exhibits bulk density in the range of about 0.5-0.6 g/ml and preferably tapped density in the range of about 0.7-0.8 g/ml.

In comparison, the N-2 form of daclatasvir dihydrochloride (Form N-2 of compound B) exhibits bulk density in the range of 0.3-0.4 g/ml and tapped density in the range of 0.4-0.5 g/ml.

These higher densities of amorphous Form C daclatasvir dihydrochloride of the present invention are advantageous in the formulation of Form C, especially in a tablet formulation. For example, Form C's higher density will give rise to a more compressible formulation (i.e. better compressibility). As such, Form C of the present invention is able to provide comparable dissolution characteristics but with the advantage of the Form C being more suitable for pharmaceutical formulation.

Accordingly, it is preferred that the Form C of the present invention is characterized by a bulk density in the range of about 0.5-0.6 g/ml. Further it is preferred that the Form C of the present invention is characterized by a tapped density in the range of about 0.7-0.8 g/ml.

The amorphous nature of Form C of compound B has been analyzed, characterized and differentiated by X-ray powder diffraction, a technique which is known per se.

Preferably, the amorphous Form C of compound B of the present invention is characterized by having an X-ray powder diffraction spectrum as shown in FIG. 2.

Preferably, the amorphous Form C of compound B of the present invention is characterized by its X-ray diffraction pattern comprising an amorphous halo. Preferably, its X-ray diffraction pattern does not comprise any sharp (or distinct) characteristic peaks.

The amorphous Form C of compound B according to (or obtained by) the present invention is substantially free (or free or essentially free) from other crystal and non-crystal forms of compound B, for example free from crystalline forms of compound B. "Substantially free from other forms of compound B" or "Essentially free from other forms of compound B" shall be understood to mean that the polymorph of compound B contains less than about 10%, 9%, 8%, 7%, 6% or preferably less than about 5%, of any other forms of compound B (for example crystalline forms) and preferably less than about 1% of other impurities, water or solvates.

Those skilled in the art would recognize that amorphous Form C may be characterized by other methods including, but not limited to IR, solid state NMR and Raman spectroscopy.

The amorphous Form C of compound B of the present invention was further characterized by IR spectroscopy. This was carried out on a Bruker Model: Alpha Fourier Transform Infrared (FTIR) Spectrometer.

Figure 5:
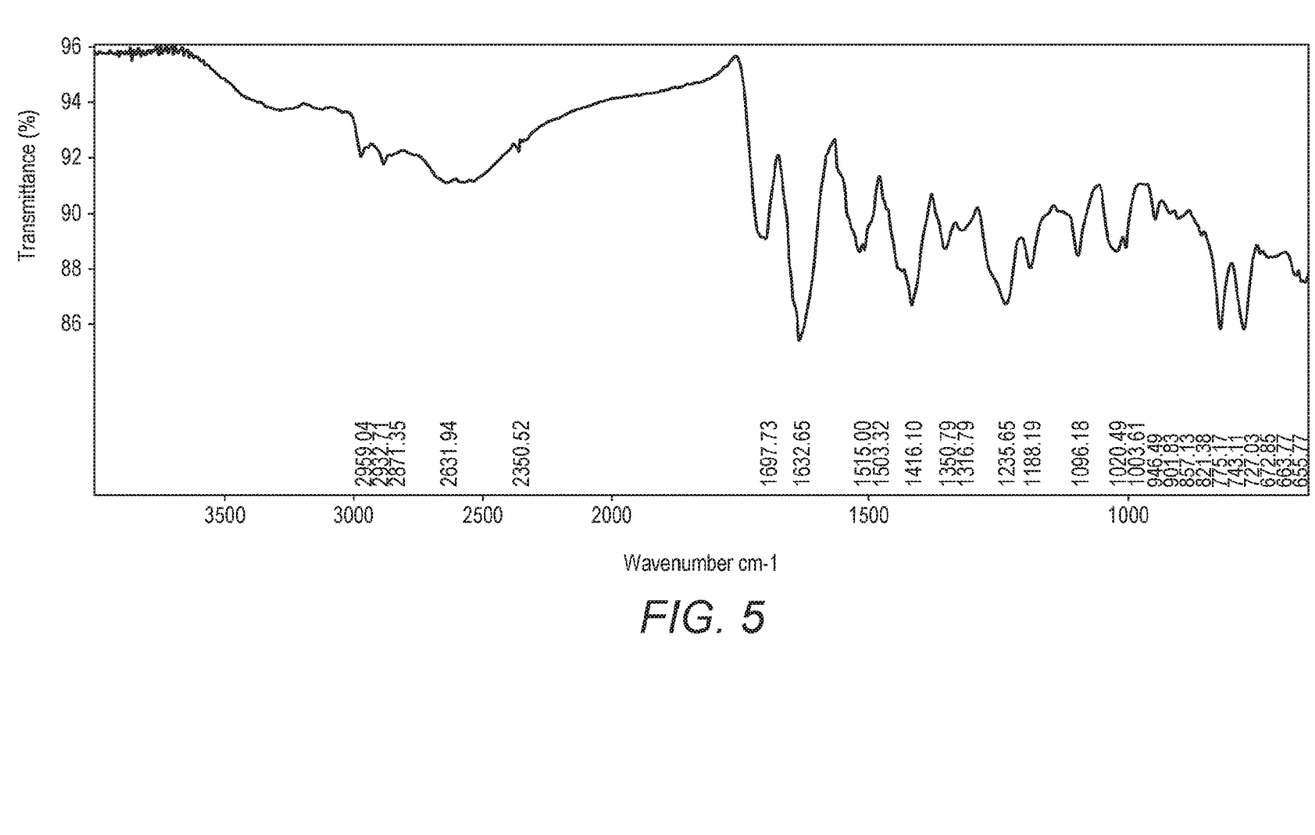
FIG. 5 is the Fourier Transform Infrared (FTIR) spectrum of amorphous Form C of compound B.

Accordingly, the amorphous Form C of compound B of the present invention can be characterized as having a FTIR spectrum as shown in FIG. 5.

Pharmaceutical compositions according to the present invention comprise amorphous Form C of Compound B as an active ingredient together with one or more pharmaceutically acceptable carriers, excipients or diluents In another aspect, the present invention provides a process for preparing the novel amorphous Form C of compound B. Preferably, Form C of compound B is solvate-free.

The process produces amorphous Form C of compound B with high yield and purity.

Amorphous Form C may be prepared by a process (method C1) comprising the steps of:

i. condensing MOC-L-Valine with DCV imidazole HCl using condensing reagent or mixture of condensing reagents thereof, preferably in a suitable inert organic solvent in a suitable base at a suitable temperature,
ii. adding a first solvent,
iii. separating the organic layer, for example by washing with NaCl and NaOH solutions
iv. optionally filtering, preferably over hyflo, and optionally washing with the first solvent, the distilled filtrate then optionally being distilled under reduced pressure
v. optionally drying, preferably over a drying agent,
vi. treating with HCl at a suitable temperature, preferably ranging from about −5° C. to about 40° C.
vii. stirring for a suitable amount of time, preferably about 30 minutes to about 5 hours at a temperature of about −5° C. to about 40° C.,
viii. isolating the precipitated amorphous Form C of compound B, preferably washed with a suitable solvent such as ethyl acetate and,
ix. drying the precipitated amorphous Form C.

Amorphous Form C may also be prepared by a process (method C2) comprising the steps of:

i. dissolving compound A of any form, or in a mixture of any forms, in a first solvent, preferably under an inert atmosphere,
ii. treating with HCl at a suitable temperature, preferably ranging from about −5° C. to about 40° C.,
iii. stirring for a suitable amount of time, preferably about 30 minutes to about 5 hours at a temperature of about −5° C. to about 40° C., preferably at about room temperature
iv. isolating the precipitated amorphous Form C of compound B, preferably washed with a suitable solvent such as ethyl acetate and,
v. drying the precipitated amorphous Form C.

Amorphous Form C may also be prepared by a process (method C3) comprising the steps of:

i. dissolving crystalline compound B of N-2 or N-1 form or any form or in a mixture of any forms, in a first solvent, preferably at a suitable temperature, such as about 50-70° C.,
ii. adding a second solvent,
iii. stirring for a prolonged time period, preferably for about 30 minutes to 4 hours, preferably about 1 to 2 hours
iv. isolating the precipitated amorphous Form C of compound B, preferably washing with a suitable solvent such as ethyl acetate and,
v. drying the precipitated amorphous Form C.

Amorphous Form C may also be prepared by a process (method C4) comprising the steps of:

i. dissolving crystalline compound B of N-2 or N-1 form or any form or in a mixture of any forms, in a first solvent, and optionally adjusting the pH of the reaction mass using a base
ii. adding a second solvent to extract the reaction mass,
iii. optionally separating the organic layer and optionally drying, preferably with a drying agent to obtain a clear filtrate,
iv. adding HCl to the clear filtrate
v. isolating the precipitated amorphous Form C of compound B, preferably washing with a suitable solvent such as ethyl acetate and,
vi. drying the precipitated amorphous Form C.

The first solvent that can be used for dissolution in these preparations include water; alcohols comprising methanol, ethanol, isopropanol, N-butanol; ketones comprising acetone, methyl ethyl ketone; chloroalkanes, comprising dichloromethane (MDC); alkyl alkanoates comprising methyl acetate, ethyl acetate, butyl acetate, isopropyl acetate and a mixture thereof. Preferably the first solvent is an alcohol, a ketone, a chloroalkane, an alkyl alkanoate or any combination thereof. More preferably the solvent is alkyl alkanoate, an alocohol or any combination thereof. Most preferably, the first solvent is water, isopropyl acetate, ethyl acetate or methanol.

The second solvent used may be same as the first solvent or an anti solvent wherein the anti solvent is selected from esters such as ethyl acetate or isopropyl acetate, dialkyl ethers comprising diisopropyl ether, methyl t-butylether; aromatic hydrocarbons comprising toluene, xylene, and aromatic chlorohydrocarbons comprising chlorobenzene, 1,2-dichlorobenzene, dichloromethane; hydrocarbons comprising n-pentane, n-hexane, n-heptane, cyclopentane, cyclohexane and a mixture thereof. Preferably the second solvent is the same as the first solvent or is a dialkyl ether, an aromatic hydrocarbon, an ester, an aromatic chlorohydrocarbon, a hydrocarbon or any combination thereof. More preferably, the second solvent is ethyl acetate.

A suitable condensing reagent for use in a process according to the present invention can be selected from the group comprising of phenylsilane, 1,1'-carbonyldiimidazole (CDI), benzotriazol-1-yloxytris (dimethylamino) phophonium hexafluorophosphate (BOP), 1-hydroxy benzotriazole hydrate (HOBt), PyBOP (Analog of the BOP), 1,3-dicyclohexylcarbodiimide (DCC), N-Ethyl-N'-(3-dimethylaminopropyl)carbodidimide hydrochloride (EDC HCl), (1-[Bis(dimethyl amino) methylene]-1H-1,2,3-triazolo[4,5-b]pyridinium 3-oxid hexafluoro phosphate) (HATU), chloroformates such as ethyl chloroformate or isobutyl chloroformate. These agents act in situ as activating reagents and convert the carboxylic acids to more reactive intermediates. Alternatively, phenylsilane, SOCl2, POCl3 and PCl3 can act as an in situ carboxylic acid activating agents, and can be effectively used as a coupling reagent to prepare carboxamides. Preferably the condensing agent is HOBt and/or EDC HCl.

By "inert organic solvent" is meant an organic solvent, which under the reaction conditions of a process according to the present invention, does not react with either the reactants or the products. A suitable inert organic solvent for use in a process according to the present invention can be selected from the group consisting of dimethylformamide (DMF), dimethylacetamide (DMA), dimethyl sulfoxide (DMSO), N-methyl pyrrolidone (NMP), sulfolane, diglyme, 1,4-dioxane, tetrahydrofuran (THF), acetonitrile, acetone, dichlromethane (MDC), toluene, xylene and any combination thereof and other inert organic solvents known in the art. Preferably the "inert organic solvent" is acetonitrile or DMF.

A suitable base to be used in a process of the present invention may be an organic base and/or an inorganic base. Preferably the organic base is an aliphatic or aromatic organic base and preferably the inorganic base is a alkali metal carbonate, alkali metal alkoxide or alkali metal hydroxide inorganic base and any combination thereof.

Suitable organic bases can be selected from the group comprising of aliphatic or aromatic bases and can be selected from, but not limited to triethyl amine, diisopropyl amine, diisopropyl ethyl amine, pyridine, picoline, diethyl amine, piperidine and any combination thereof. Preferably the organic base is diisopropyl ethyl amine.

Suitable inorganic bases can be selected from the group comprising of ammonia, alkali metal carbonates, such as cesium carbonate, sodium carbonate, sodium bicarbonate, potassium carbonate; alkali metal alkoxide such as sodium methoxide, sodium ethoxide, potassium tertiary butoxide; alkali metal hydroxides such as sodium hydroxide, potassium hydroxide and any combination thereof.

The base used for adjusting the pH in method C4 above would be an inorganic base as mentioned above, preferably ammonia. The pH would also preferably be adjusted to between about 6 and 9, preferably about 7.5.

The condensation is suitably carried out at a temperature ranging from about 5° C. to the boiling point of the reaction mass until no starting material is detectable. Preferably, the temperature is about 5 to 30° C., preferably about 20 to 30° C. or about 10 to 15° C. Preferably, the condensing is carried out under a nitrogen atmosphere.

The drying agents that can be used for the removal of water include but not limited to anhydrous sodium sulphate, anhydrous magnesium sulphate, anhydrous zinc chloride and anhydrous calcium chloride. Preferably, the drying agent is anhydrous sodium sulphate.

The HCl may be added in the form of a solution in the first solvent or in the form of a solution in the second solvent or as a gas. Preferably the HCl is added in the form of a solution in the first or second solvent, for example ethyl acetate.

The isolation may be carried out by filtering, decanting or centrifuging.

The final drying step is preferably carried out at a temperature preferably ranging from about 30 to 80° C., preferably from about 30 to 70° C., more preferably about 45 to 65° C., typically for a period of time ranging from about 2 to 30 hours, preferably about 4 to 24 hours. Further, the final drying step is preferably carried under reduced pressure, for example in a vacuum.

For each of these methods, the fraction of drug substance (Form C) that is amorphous is in the range of about 50% w/w to about 100% w/w, 75% w/w to about 100% w/w, 90% w/w to about 100% w/w, or about 95% w/w to about 100% w/w, based on the total mass of compound B. Ideally, the fraction of compound B that is amorphous is in the range of about 99% w/w to about 100% w/w, based on the total mass of compound B.

The process of the present invention may be used as a method for purifying any form of compound B, as well as for the preparation of the new polymorphic forms of compound B or pharmaceutically acceptable salts thereof of compound A.

Thus, another aspect of the present invention is directed to the use of amorphous Form C of compound B, as a starting material for the preparation of the crystalline compound B in either anhydrous, hydrated or solvated form.

Accordingly, crystalline Form N-2 of compound B may be prepared by a process (method B1) comprising the steps of:

i. dissolving Form C of the present invention in a polyether such as polyethylene glycol (PEG) at a suitable temperature, such as about 50-65° C.
ii. cooling the reaction mass,
iii. adding a suitable solvent, such as acetone,
iv. isolating the precipitated crystalline Form N-2 of compound B, preferably washing with a suitable solvent such as acetone and,
v. drying the precipitated crystalline Form N-2 of compound B.

Compounds A and B have been found to be effective for the treatment of chronic hepatitis C virus (HCV) infection in adults. Pharmaceutical compositions according to the present invention comprise amorphous Form A of compound A or amorphous Form C of Compound B as an active ingredient together with one or more pharmaceutically acceptable carriers, excipients or diluents. Any conventional technique may be used for the preparation of pharmaceutical compositions according to the invention.

In another aspect, there is provided methyl((1 S)-1-(((2S)-2-(5-(4'-(2-((2S)-1-((2S)-2-((methoxycarbonyeamino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate as described herein for use in medicine.

In a further aspect, there is provided methyl((1S)-1-(((2S)-2-(5-(4'-(2-((2S)-1-((2S)-2-((methoxycarbonyeamino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate as described herein for use in the treatment of the hepatitis C virus.

In a further aspect, there is provided M=methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate as described herein for use in the manufacture of a medicament for treating the hepatitis C virus.

In a further aspect, there is provided a method of treating the hepatitis C virus, comprising administering a therapeutically effective amount of methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate as described herein to a patient in need thereof.

In a further aspect, there is provided the use of methyl((1 S)-1-(((2S)-2-(5-(4'-(2-((2S)-1-((2S)-2-((methoxycarbonyeamino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate as described herein in the manufacture of a medicament for the treatment of the hepatitis C virus.

In a further aspect, there is provided free base of amorphous Form A of methyl((1 S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate prepared according to any of the processes described herein.

In a further aspect, there is provided the dihydrochloride salt of amorphous Form C of Methyl((1 S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate prepared according to any of the processes described herein.

In a further aspect, there is provided methyl((1 S)-1-(((2S)-2-(5-(4'-(2-((2S)-1-((2S)-2-((methoxycarbonyeamino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate substantially as herein described with reference to the Examples and a process substantially as herein described with reference to the examples.

The invention is further described with reference to the following examples, which set forth in detail certain aspects and embodiments of the preparation of compounds and compositions of the present invention. It will be apparent to those skilled in the art, that many modifications, both to materials and methods, can be practiced without departing from the purpose and intent of this invention. The examples that follow are not intended to limit the scope of the invention as described herein above or as claimed below.

EXAMPLES

Example 1

Preparation of Amorphous Form a of Compound A

MOC-L-Valine (8 g), HOBT Monohydrate (7 g) and EDC.HCl (8.8 g) were stirred in 125 mL of acetonitrile at 10-15° C. under nitrogen for 1 hour. DCV Imidazole HCl (10 g) and Hunigs base (9.5 g) were added. The reaction mass was further stirred for 2-3 hours and 60 mL of isopropyl acetate was added. The organic layer was separated and washed with 60 mL of 13 wt % aqueous NaCl solution, 2×120 mL of 0.5 N NaOH solution containing 13 wt % aqueous NaCl solution followed by 60 mL of 13 wt % aqueous NaCl solution. The organic layer was treated with charcoal (1.5 g) and silica gel (1.5 g) for 30 minutes at room temperature. The reaction mass was filtered on hyflo, washed with isopropyl acetate. The clear filtrate was distilled under reduced pressure, stripped off with n-Heptane and dried in a vacuum oven at 40-45° C. for 4 hours to obtain amorphous Form A.

Yield—10.5 g

Example 2

Preparation of Amorphous Form C of Compound B

MOC-L-Valine (8 g), HOBT Monohydrate (7 g) and EDC.HCl (8.8 g) were stirred in 125 mL of acetonitrile at 10-15° C. under nitrogen for 1 hour. DCV Imidazole HCl (10 g) and Hunigs base (9.5 g) were added. The reaction mass was further stirred for 2-3 hours and 60 mL of isopropyl acetate was added. The organic layer was separated and washed with 60 mL of 13 wt % aqueous NaCl solution, 2×120 mL of 0.5 N NaOH solution containing 13 wt % aqueous NaCl solution followed by 60 mL of 13 wt % aqueous NaCl solution. The organic layer was treated with charcoal (1.5 g) and silica gel (1.5 g) for 30 minutes at room temperature. The reaction mass was filtered on hyflo, washed with isopropyl acetate. The clear filtrate was distilled under reduced pressure to 2 volumes. A 15 mL solution of hydrochloric acid in ethyl acetate was added slowly. The reaction mass was cooled to room temperature and further stirred for 1 hour. The solid was isolated by filtration, washed with ethyl acetate and dried in a vacuum oven at 65° C. for 24 hours to obtain amorphous Form C.

Yield—10.5 g

Example 3

Preparation of Amorphous Form a of Compound a in MeOH-water

Compound A (1 g) was dissolved 3 mL of methanol by heating the mixture under stirring at 60°. The solution was cooled to room temperature, 20 mL water was added and stirred for 1 hour. The solid was isolated by filtration, washed with water and dried in a vacuum oven at 45° C. for 15 hours to obtain amorphous Form A.

Yield—0.5 g

Example 4

Preparation of Amorphous Form C of Compound B from Compound A

Compound A (10 g) was dissolved under inert atmosphere in 120 mL of ethyl acetate at 35-40° C. 15 mL of hydrochloric acid solution in ethyl acetate was added slowly. The reaction mass was cooled to room temperature and further stirred for 1 hour. The solid was isolated by filtration, washed with ethyl acetate and dried in a vacuum oven at 65° C. for 24 hours to obtain amorphous Form C.

Yield—9.5 g

Example 5

Preparation of Amorphous Form a of Compound a from Compound B

Compound B (1 g) was dissolved in 20 mL of water at room temperature. The pH of the reaction mass adjusted to 7.5 with ammonia. The reaction mass was extracted with 15 mL of ethyl acetate. The organic layer was separated, washed with water, dried on sodium sulfate. The clear filtrate was distilled under reduced pressure, stripped off with n-Heptane and dried in a vacuum oven at 40-45° C. for 4 hours to obtain amorphous Form A.

Yield—0.5 g

Example 6

Preparation of Amorphous Form C of Compound B from Crystalline Form N-2 of Compound B Form N-2 of Compound B (1.0 g) B was dissolved in 3 mL of methanol at 60° C. The reaction mass was cooled to 30-35° C., 15 mL of ethyl acetate was added and the reaction mass was further stirred for 1 hour. The solid was isolated by filtration, washed with ethyl acetate and dried in a vacuum oven at 45° C. for 15 hours to obtain amorphous Form C Yield—0.7 g

Example 7

Preparation of Crystalline Form N-2 from Amorphous Form C

Amorphous Form C (1.0 g) was dissolved in 3 mL of PEG 300 by heating the mixture under stirring at 60°. The solution was cooled to room temperature, 20 mL acetone was added and stirred for 1 hour. The solid was isolated by filtration, washed with acetone and dried in a vacuum oven at 45° C. for 15 hours to obtain crystalline Form N-2.

Yield—0.5 g

Example 8

Preparation of Amorphous Form C of Compound B from Compound B

Compound B (1 g) was dissolved in 20 mL of water at room temperature. The pH of the reaction mass adjusted to 7.5 with ammonia. The reaction mass was extracted with ethyl acetate. The organic layer was separated, washed with water, dried on sodium sulfate. To the clear filtrate was added slowly a solution of 15 mL of HCl in ethyl acetate and the reaction mass was further stirred for 1 hour. The solid was isolated by filtration, washed with ethyl acetate and dried in a vacuum oven at 45° C. for 15 hours to obtain amorphous Form C.

Yield—0.5 g

Example 9

Preparation of Amorphous Form a of Compound A

MOC-L-Valine (32 g), HOBT Monohydrate (28 g) and EDC.HCl (35.2 g) were stirred in 200 mL of dimethylfomamide (DMF) at 20-30° C. under nitrogen for 1 hour. DCV Imidazole HCl (40 g) and Hunig's base (38 g) were added. The reaction mass was maintained under Nitrogen for 2 hours.

The reaction mass was quenched in 25 volumes of 2% NaOH and stirred for 30 minutes at 25-30° C. It was then filtered, washed with water and dried in a vacuum at 35-40° C. to obtain amorphous Form A.

Yield—40 g

The invention claimed is:

1. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate and pharmaceutically acceptable salt thereof in an amorphous form.

2. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate according to claim 1, further characterized in that it is in a free base form.

3. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate according to claim 1, wherein the pharmaceutically acceptable salt is the dihydrochloride salt.

4. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate according to claim 2, characterised by the XRPD pattern shown in FIG. 1.

5. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate Form A according to claim 4, further characterised by the FTIR spectrum as shown in FIG. 4.

6. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate according to claim 3, characterised by the XRPD pattern shown in FIG. 2.

7. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate according to claim 6, further characterised by the FTIR spectrum as shown in FIG. 5.

8. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate according to claim 3, characterized by an XRPD pattern comprising an amorphous halo.

9. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate according to claim 1, essentially free of crystalline forms of methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate or salts thereof.

10. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate according to claim 3, having a bulk density in the range of about 0.5-0.6 g/ml.

11. Methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate according to claim 3, having a tapped density in the range of about 0.7-0.8 g/ml.

12. A pharmaceutical composition comprising methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate as defined in claim 1 with one of more pharmaceutically acceptable carriers, excipients or diluents.

13. A process for producing amorphous methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate free base as defined in claim 2, comprising:

(a) dissolving compound A in a first solvent,

Compound A (b) optionally adding a second solvent,
(c) isolating the precipitated amorphous form and,
(d) drying the precipitated amorphous form.

14. The process according to claim 13, wherein compound A is prepared by condensing N-methoxy carbonyl-L-valine with 5,5'-(4,4'-biphenyldiyl)bis(2-((2S)-2-pyrrolidinyl)-1H-Imidazole Hydrochloride.

15. The process according to any one of claims 13, wherein the first solvent comprises a solvent selected from the group consisting of water; methanol, ethanol, isopropanol, N-butanol, acetone, methyl ethyl ketone; dichloromethane, methyl acetate, ethyl acetate, butyl acetate, isopropyl acetate and any combination thereof.

16. The process according to any one of claims 13, wherein the second solvent comprises an anti solvent selected from one or more of water, methanol, ethanol, isopropanol, N-butanol, diisopropyl ether, methyl t-butylether, toluene, xylene, chlorobenzene, 1,2-dichlorobenzene, dichloromethane, n-pentane, n-hexane, n-heptane, cyclopentane, cyclohexane and any combination thereof.

17. A process for producing amorphous methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl) carbonyl)-2-methylpropyl) carbamate dihydrochloride as defined in claims 3, comprising:

(a) dissolving compound A in a first solvent,

Compound A (b) treating with HCl,
(c) isolating the precipitated amorphous form and,
(d) drying the precipitated amorphous form.

18. A process for producing amorphous methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl) carbamate dihydrochloride as defined in claims 3, comprising:
(a) dissolving compound B in a first solvent, Compound B (b) adding a second solvent,
(c) isolating the precipitated amorphous form and,
(d) drying the precipitated amorphous form.

19. The process according to claim 17, wherein compound A is prepared by condensing N-methoxy carbonyl-L-valine with 5,5'-(4,4'-biphenyldiyl)bis(2-((2S)-2-pyrrolidinyl)-1H-Imidazole Hydrochloride.

20. The process according to claims 17, wherein the first solvent comprises a solvent selected from the group consisting of water, methanol, ethanol, isopropanol, N-butanol, acetone, methyl ethyl ketone; dichloromethane, methyl acetate, ethyl acetate, butyl acetate, isopropyl acetate and any combination thereof.

21. The process according to claims 18, wherein the second solvent comprises an anti solvent selected from the group consisting of diisopropyl ether, methyl t-butylether, toluene, xylene, chlorobenzene, 1,2-dichlorobenzene, dichloromethane, n-pentane, n-hexane, n-heptane, cyclopentane, cyclohexane and any combination thereof.

22. A process for producing amorphous methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl) carbamate free base as defined in claim 2, comprising:
(a) condensing MOC-L-Valine with DCV imidazole HCl,
(b) quenching the reaction mass,
(c) isolating the precipitated amorphous form,
(d) drying the precipitated amorphous form.

23. The process according to claim 22, wherein the condensation is carried out in the presence of one or more condensing reagents, an inert organic solvent and a base.

* * * * *

UNITED STATES PATENT AND TRADEMARK OFFICE
CERTIFICATE OF CORRECTION

PATENT NO. : 10,300,044 B2  
APPLICATION NO. : 15/538959  
DATED : May 28, 2019  
INVENTOR(S) : Dharmaraj Ramachandra Rao et al.

Page 1 of 1

It is certified that error appears in the above-identified patent and that said Letters Patent is hereby corrected as shown below:

In the Claims  
Claim 1, Column 20, Line 20, replace "salt" with --salts--.  
Claim 15, Column 22, Line 34, replace "any one of claims 13," with --claim 13,--.  
Claim 16, Column 22, Line 40, replace "any one of claims 13," with --claim 13,--.

Signed and Sealed this  
Sixteenth Day of July, 2019

Andrei Iancu  
*Director of the United States Patent and Trademark Office*